(12) United States Patent
Foster

(10) Patent No.: US 6,838,056 B2
(45) Date of Patent: Jan. 4, 2005

(54) METHOD AND APPARATUS FOR SORTING BIOLOGICAL CELLS WITH A MEMS DEVICE

(75) Inventor: John Stuart Foster, Santa Barbara, CA (US)

(73) Assignee: Innovative Micro Technology, Goleta, CA (US)

(*) Notice: Subject to any disclaimer, the term of this patent is extended or adjusted under 35 U.S.C. 154(b) by 155 days.

(21) Appl. No.: 10/189,607

(22) Filed: Jul. 8, 2002

(65) Prior Publication Data

US 2004/0005628 A1 Jan. 8, 2004

(51) Int. Cl.$^7$ .............................. G01N 1/10; C12M 1/34
(52) U.S. Cl. ................. 422/100; 422/82.01; 422/82.05; 422/82.08; 436/43; 436/46; 436/63; 436/149; 436/164; 436/165; 436/172; 436/180; 435/29; 435/30; 435/287.1; 435/288.3; 435/288.4; 435/288.5; 435/288.7; 209/3.1; 209/552; 209/576
(58) Field of Search .............................. 436/43, 46, 63, 436/149, 150, 164, 165, 172, 177, 180; 422/68.1, 73, 82.01, 82.05, 82.08, 100, 101, 103; 435/29, 30, 287.1, 288.3, 288.4, 288.5, 288.7, 287.2, 7.1; 209/3.1, 552, 576

(56) References Cited

U.S. PATENT DOCUMENTS 5,837,200 A * 11/1998 Diessel et al. ................. 422/73
5,971,355 A * 10/1999 Biegelsen et al. ......... 251/129.06
6,303,885 B1 * 10/2001 Hichwa et al. ............... 200/181
6,593,749 B2 * 7/2003 Foster et al. ................. 324/514
6,692,952 B1 * 2/2004 Braff et al. .............. 435/288.4

FOREIGN PATENT DOCUMENTS

WO 01/19516 * 3/2001

OTHER PUBLICATIONS

Gawad et al. Lab on a Chip, vol. 1, 2001, pp. 76–82.*
Blankenstein et al. Biosensors and Bioelectronics, vol. 13, Nos. 3–4, 1998, pp. 427–438.*
Fu et al. Analytical Chemistry, vol. 74, No. 11, Jun. 1, 2002, pp. 2451–2457.*
Baechi et al. Sensors and Actuators A, vol. 95, Jan. 1, 2002, pp. 77–83.*

* cited by examiner

Primary Examiner—Maureen M. Wallenhorst

(57) ABSTRACT

A micromechanical actuator for sorting hematopoietic stem cells for use in cancer therapies. The actuator operates by diverting cells into one of a number of possible pathways fabricated in the fabrication substrate of the micromechanical actuator, when fluorescence is detected emanating from the cells. The fluorescence results from irradiating the cells with laser light, which excites a fluorescent tag attached to the cell. The micromechanical actuator thereby sorts the cells individually, with an operation rate of 3.3 kHz, however with the massively parallel 1024-fold device described herein, a throughput of 3.3 million events/second is achievable.

9 Claims, 5 Drawing Sheets

METHOD AND APPARATUS FOR SORTING BIOLOGICAL CELLS WITH A MEMS DEVICE

FIELD OF THE INVENTION

This invention relates to the sorting of biological cells. More particularly, this invention relates to the use of a MEMS device for performing the sorting by physically separating the component of interest from the rest of the fluid sample.

BACKGROUND OF THE INVENTION

Many new therapies for cancer patients relate to enabling them to better withstand the challenge made to their bodies by the chemotherapies. In particular, it has recently been found that the inability of some patients to cope with chemotherapies has to do with the destruction of hematopoietic stem cells (HSCs), as ancillary damage of the chemotherapy. HSCs are the progenitor cells found in bone marrow, peripheral blood and many lymphoid organs. HSCs are responsible for generating the immune system components, such as T-cells, as well as the vital components of blood. When HSCs are destroyed in sufficient numbers, it becomes difficult for patients to replace blood cells, resulting in anemia often suffered by patients. The destruction of HSC's is also a leading cause of death in radiation victims, as the progenitor cells are destroyed, thereby destroying the ability to regenerate the vital components of the blood and immune systems.

Recent research has indicated however that if the HSCs are removed from the patients' bodies prior to their receiving chemotherapy, and then replaced after the chemotherapy, the HSCs are shielded from the effects of the chemotherapy. By reinfusing the HSCs after the chemotherapy is finished, the patients' ability to regenerate their blood cells is regained and their resilience to the therapy is greatly enhanced. As a result, higher dosages of the chemotherapy can be administered to patients with better chances of diminishing the viability of the cancer cells, and yet the patients are able to regraft their blood-forming HSCs, which have been protected from exposure to the chemotherapy.

Until recently, the standard treatment for patients requiring blood-forming system reconstitution after chemotherapy was a bone marrow transplant (BMT). Bone marrow transplants require up to 100 withdrawals of marrow from the hip bone by large needles and the subsequent reinfusion of large volumes of cells and other fluid. These procedures are highly invasive, cumbersome, expensive and pose additional risks to the patient.

Mobilized peripheral blood (MPB), which accomplishes the same post-chemotherapy reconstitution with less trauma to the donor, can be generated in most patients by injecting a granulocyte colony-stimulating factor (G-CSF) that causes the body to produce a sufficient quantity of hematopoietic stem cells (HSCs). These cells migrate from the bone marrow to the blood, from which they are harvested in a sufficient quantity in a single 2–4 hour session that only requires vein access.

Both the bone marrow extractions and mobilized peripheral blood from cancer patients contain the hematopoietic stem cells necessary for reconstitution; however, they also contain large numbers of cancer cells, which are reinfused into the patient along with the HSCs after the chemotherapy treatment. Logic and an increasing body of literature suggest that this reintroduction of cancer cells is one cause of the limited survival improvement associated with high dose chemotherapy and cell transplant.

Therefore, technology was developed to obtain highly purified non-cancerous HSCs from mobilized peripheral blood; i.e., the purification process eliminates the cancer cells, but retains the healthy stem cells necessary for reconstitution. The purification process also reduces the transfusion volume to less than 0.1 ml, in contrast to the 500–1500 ml of cells in fluid volume for BMT and MPB. The purification process is performed by flow cytometry, which separates the constituents of a fluid sample mixture according to fluorescence detected from the constituents. Purity of the resulting HSC product was 95% by this method, with no detectable cancer cells, and further details of the methodology can be found in Negrin et al., "Transplantation of Highly Purified $CD34^+Thy-1^+$ Hematopoietic Stem Cells in Patients with Metastatic Breast Cancer", Biology of Blood and Marrow Transplantation 6:262–271 (2000). For patients undergoing this HSC reinfusion treatment, the 5-year survival rate for women with advanced metastatic breast cancer rose from 5% to about 50%.

Another application for HSC sorting is protection against nuclear radiation effects. The procedure would be to sort HSCs from individuals who potentially could be exposed at some later date to nuclear radiation. The HSCs are frozen and can survive in that state essentially forever. If the individual is exposed, as could be the case in a nuclear plant accident or warfare, the HSCs are then shipped to the patient's location, rapidly thawed, and then re-inserted into the patient. This procedure has been shown to save animals exposed to otherwise lethal doses of radiation.

However for these treatments to become practical, it must be learned how to sort large quantities of viable hematopoietic stem cells from the other constituents of the blood, with high concentration and high purity. An estimate of the number of stem cells required is $4 \times 10^6$ stem cells/kg body weight. The present separation process, flow cytometry, uses a high-pressure nozzle to separate tiny droplets containing the cells. The cell suspension is brought to the nozzle assembly under positive pressure, and introduced to the center of the sheath flow. The properties of fluid laminar flow focus the cell suspension into a single file, which is confined to the center of the fluid jet. Droplets are formed as the fluid exits the nozzle, and the droplets pass through one or more laser beams, which irradiate the cells and excite fluorescent markers with which the cells are tagged. The droplets are then given an electric charge to separate the droplets containing HSCs from those containing other constituents of the blood, as detected by fluorescence of the tagged molecules. The droplets are separated by passing them between a pair of electrostatic plate capacitors, which deflect the charged droplets into a sorting receptacle. The time-of-flight of the droplet through these stages requires careful calibration so that the sorting efficiency and effectiveness can be optimized.

Among the difficulties with the process is speed, as throughputs are limited to about 40,000 events per second. The rate is limited by the amount of pressure that the cells can withstand without damaging their viability, and the flow rate is proportional to the pressure. The fluidic settings which control the conditions of operation of the flow cytometers are interrelated. The nozzle diameter, system pressure and droplet frequency are independently set, whereas the jet velocity is related to the system pressure and nozzle diameter. The droplet time-of-flight must be set by empirical calibration with a standard sample. Therefore, not only are the systems themselves quite expensive, they require trained engineering staff to operate effectively. And lastly, contamination of the vessels with old sample material is a problem, as the equipment is difficult to sterilize. Decontamination issues encourage the use of disposable vessels, for which these machines are presently not designed. The high pressures used in the machines favor permanent fixturing of the plumbing in the tools. Also the careful alignment required of the receptacles with the trajectories of the droplets favors the permanent installation of the receptacles. About 7000 such systems exist worldwide today, and tend to be research tools rather than production equipment which can be used for clinical sorting in treating patients.

Therefore a need exists for a separation technique that solves throughput, cost, and disposability issues associated with present methods. This disclosure describes a novel device and method based on microelectrical mechanical systems (MEMS). MEMS devices are micron-sized structures which are made using photolithographical techniques pioneered in the semiconductor processing industry. Due to their small size and the batch fabrication techniques used to make the structures, they are capable of massive parallelism required for high throughput. These same features make them relatively inexpensive to fabricate, so that a disposable system is a realistic target for design.

BRIEF DESCRIPTION OF THE DRAWINGS

The present invention will be understood more fully from the following detailed description, and from the accompanying drawings, which however, should not be taken to limit the invention to the specific embodiments shown but are for explanation and understanding only.

DETAILED DESCRIPTION

Figure 1:
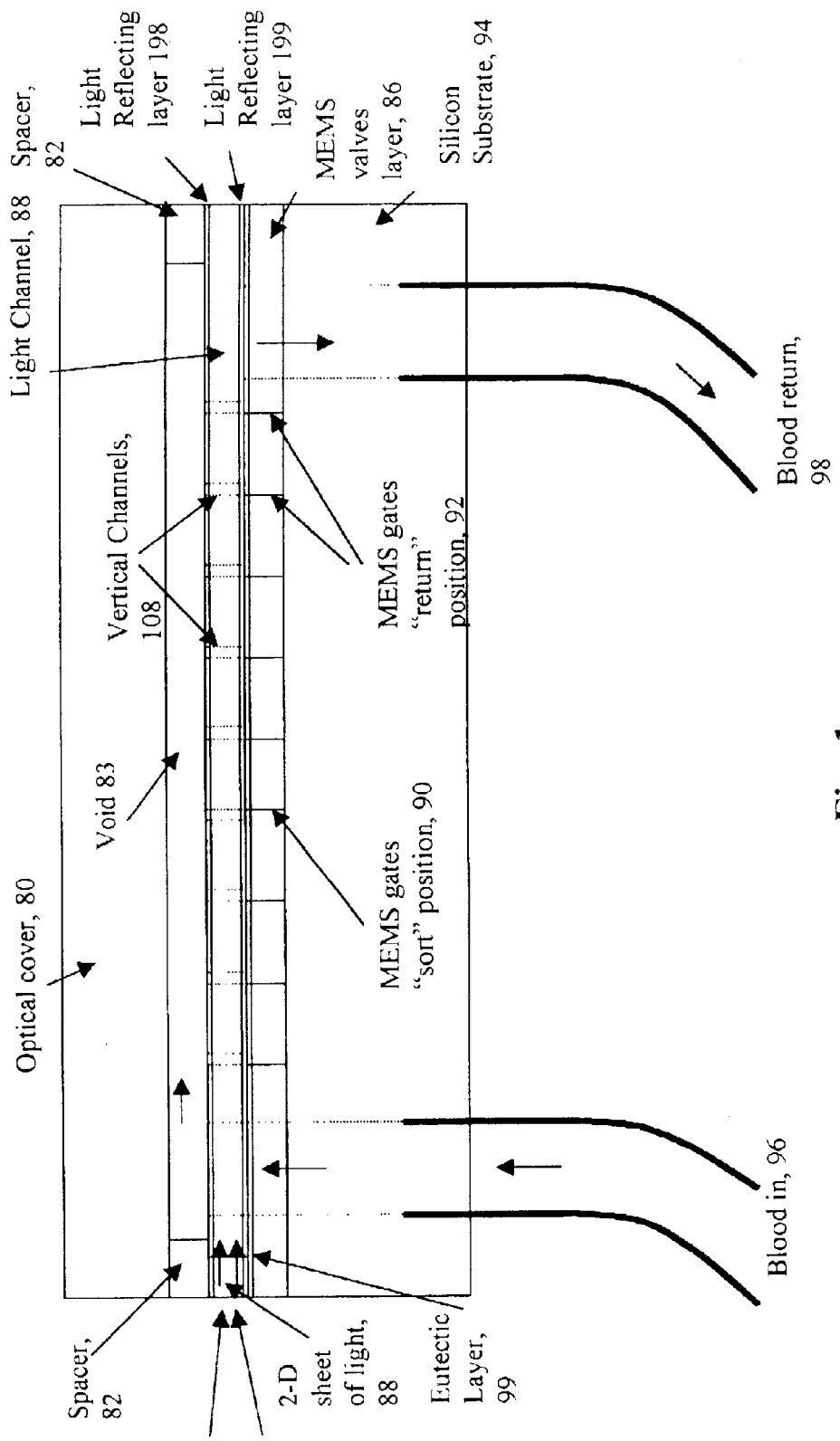
FIG. 1 is a simplified side view of the MEMS cell sorter chip, showing the light channel layer and reflective layers in detail.

The MEMS device is an array of 1024 vertical inlet channels fabricated in a wafer, wherein the 25 um diameter of each channel is just large enough to admit the passage of a hematopoietic stem cell. (Hematopoietic stem cells are typically between 5 and 10 um in diameter.) At the exit from each vertical channel is an independent valve/actuator. The actuator directs the cells individually into one of two of different possible pathways, which are microfluidic channels etched into the wafer, beneath the vertical inlet channels. The situation is shown schematically in FIG. 1. The figure shows the application of the device to the separation of the components of human blood, in this case the separation of hematopoietic stem cells (HSCs) from a fluid mixture of other cells. The actuator separates the sample stream into one of two manifolds, depending on the detection of a laser-induced fluorescence signal or multiple signals, depending on the fluorescent markers used. The presence of fluorescence or multiple fluorescence indicates that an HSC is detected, and the actuator directs the cell into a stem cell manifold with its stem cell receptacle. The receptacle contains a cushion of fresh serum for sustaining viability of the cells collected.

The use of fluorescent markers to tag biological cells is known in the art. A wide variety of fluorescent markers exist which may be conjugated as labels to antibodies specific to cellular markers which identify particular sets and subsets of cells. Fluorescent markers which are available include fluorescein, Texas Red, phycobiliproteins, cyanine derivatives and rhodamine. For example, Negrin et al. ("Transplantation of Highly Purified CD34+Thy-1+ Hematopoietic Stem Cells in Patients with Metastatic Breast Cancer", Biology of Blood and Marrow Transplantation 6:262–271 (2000)) reported that simultaneous detection of antigens CD34 and Thy-1 have good correlation to the presence of human HSCs. The lack of fluorescence indicates the cell is another constituent of the mixture, and not the tagged component. The occurrence of fluorescence indicates that the component of interest is present. In the case of detection of multiple fluorescent markers simultaneously, in some cases more than one laser may be used to excite the markers.

The sample cells are dispersed in any convenient medium which can maintain viability such as phosphate-buffered saline, containing 0.1% to 0.5% fetal calf serum. The cells may have been subjected to pre-treatment, such as removal of cells by centrifugation, affinity separation or other technique which provides enrichment of the population of cells of interest. In addition, the cells may be diluted to avoid cells being concentrated too close to each other. The fluid mixture is then introduced to the MEMS device under positive pressure, through the inlet via 96, and out through the outlet via 98. The positive pressure is chosen to select the proper flow rate through the MEMS chip, and can be set and fixed for the duration of the use of the chip. The MEMS chip wafer includes an optical cover 80 which is a barrier to the fluid mixture as well as an optically transparent element which allows the fluorescent signals to leave the chip and be detected outside the chip. Spacer layer 82 separates optical cover 80 from light channel 88, and defines the thickness of the channel through which the fluid mixture flows before it enters the laser light/blood cell interaction zone and vertical flow channel, 108.

As the fluid mixture enters through the inlet via, it floods the void 83 which lies between the optical cover 80 and the light channel 88. The light channel 88 is made of glass (typically $SiO_2$) as shown in FIG. 1. Light channel 88 is sandwiched between two reflecting layers, light reflecting layers 198 and 199. The function of the light channel is to guide laser light in a quasi-two-dimensional sheet, exposing the cells in the fluid mixture only as the cells fall into the vertical channels 108. The fluid mixture flows from the void 83 into the 1024 vertical channels. The vertical channels have been formed in the light channel 88 by lithographic patterning and etching, and provide a region 108 for interacting with the laser light before the fluid mixture enters valve layer 86. In region 108, the cells interact with the laser beam, and the cells of interest, which have been appropriately tagged with fluorescent markers, fluoresce as a result. The fluorescence is detected outside the MEMS chip and the fluorescing cell is mechanically separated from the other cells in the mixture, by the action of the electrostatic MEMS actuator. The valve labeled 90 is in the sort/save position corresponding to the presence of an HSC, whereas the valves labeled 92 are in the waste position.

Figure 2:
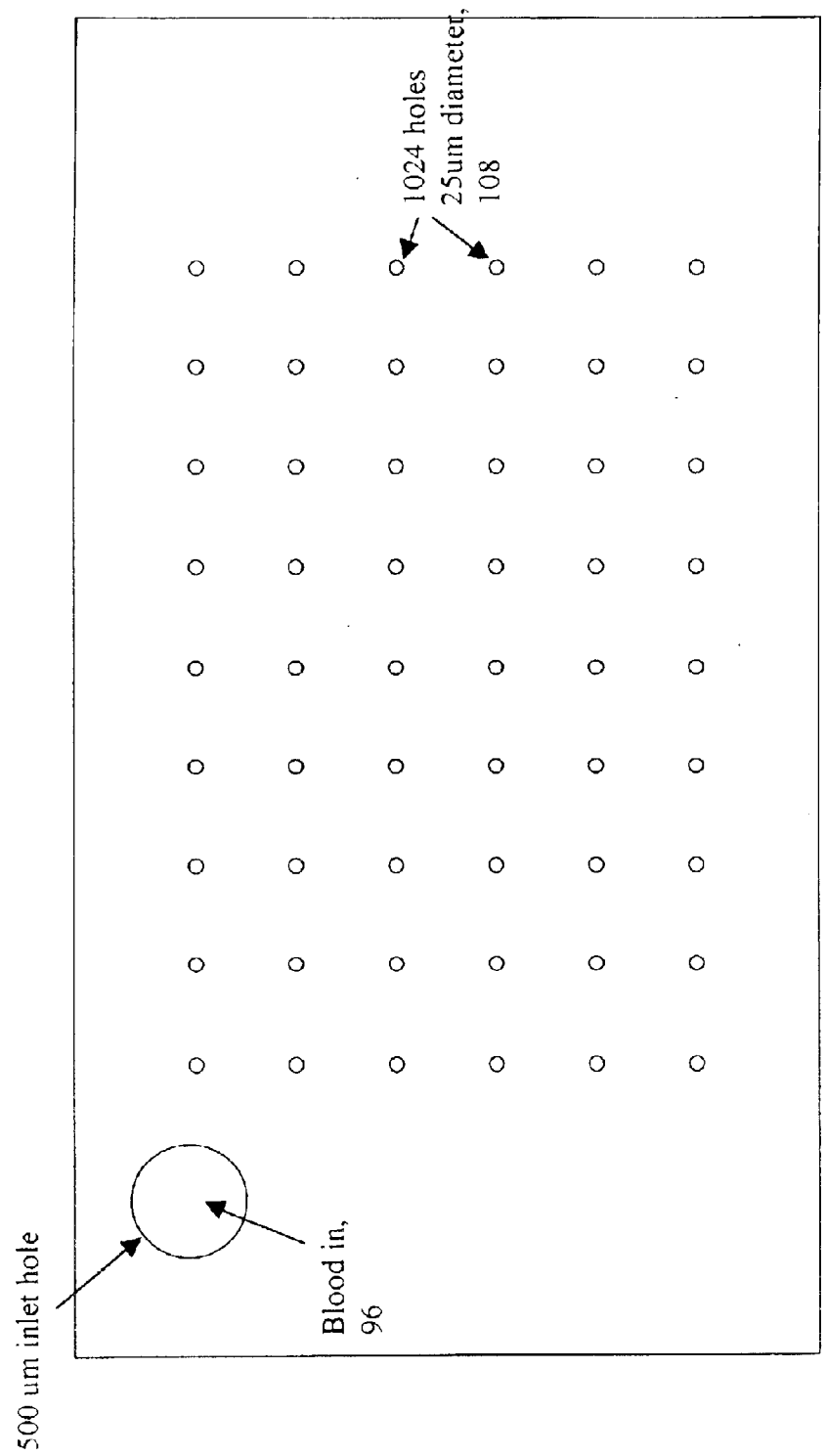
FIG. 2 is a plan view of the top surface of the MEMS cell sorter chip, showing the optically transparent light channel layer, as seen through the optical cover.
Figure 3:
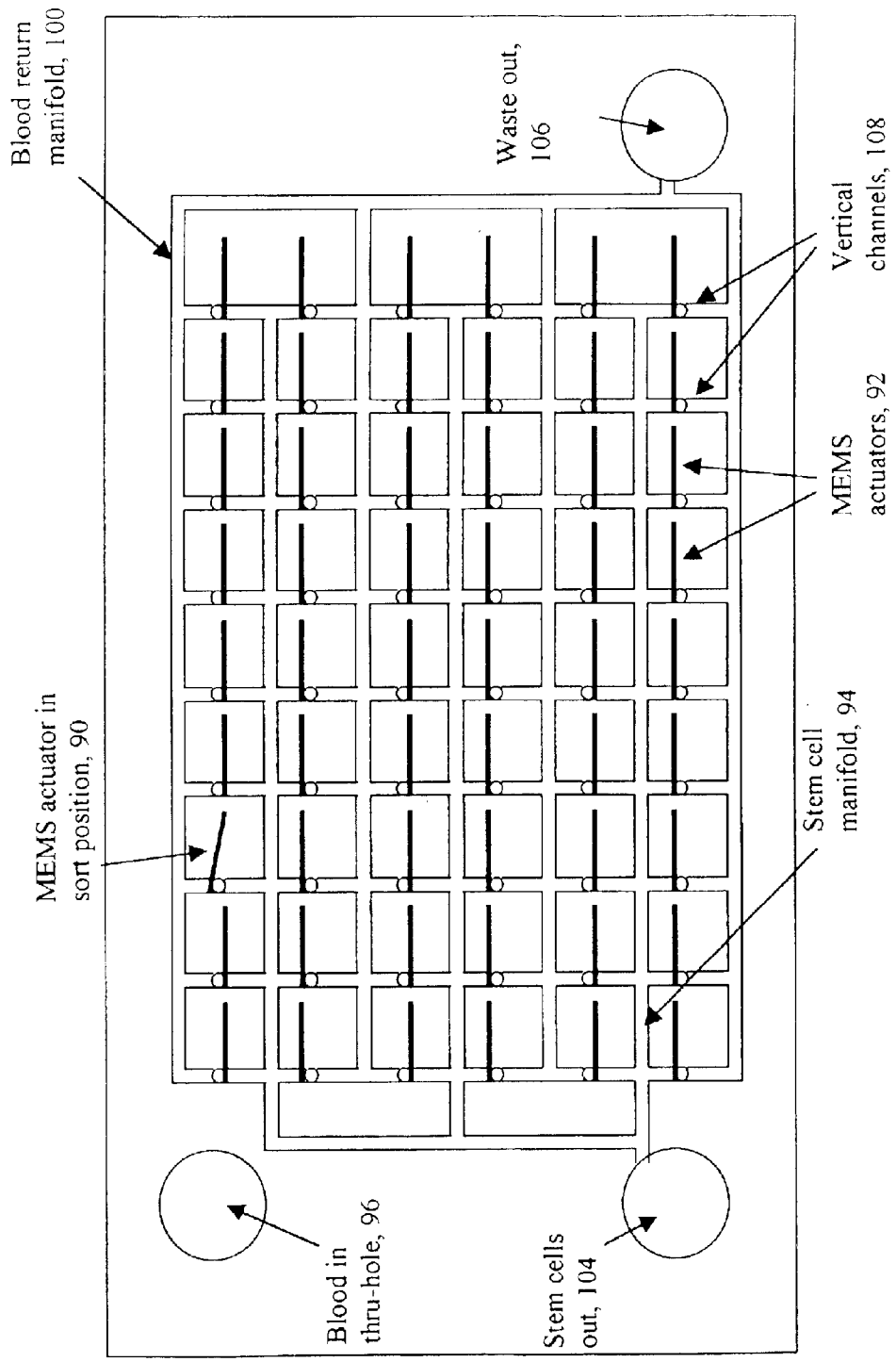
FIG. 3 is a plan view of the actuator/manifold layer of the MEMS cell sorter chip, showing the sorting manifolds.

The top view of light channel 88 is shown in detail in FIG. 2, including the vertical channels, 108. The sample mixture is delivered to the top surface of FIG. 2 by the inlet via, 96, from which it filters down through the vertical channels 108 to the actuator/manifold layer. The manifold and actuator layer is shown in FIG. 3, and it lies just beneath the optically transparent layer. The actuators are shown diagrammatically as the plurality of structures 92, lying at the exit of each vertical channel. As in FIG. 1, each of the actuators 92 shown is in the "waste" or "return" positions, directing the cells into the blood return manifold 100, with the exception of actuator 90, which is in the sort/save position. This actuator directs a fluorescing cell into the stem cell manifold 94, and the remaining actuators 92 direct non-fluorescing cells into the blood return manifold 100. After being properly herded into the stem cell manifold, the cell follows the fluid stream under positive pressure, until it reaches the stem cell out tube 104 leading to the stem cell receptacle, or the waste out tube 106 leading to the waste receptacle if it is a non-fluorescing cell. The dual manifolds have been patterned in the MEMS substrate, by lithographic means, as is shown in FIG. 3. The manifolds are sealed at the top by eutectic layer 99, which lies between bottom light reflecting layer 199 and the MEMS valves layer 86.

The timing of fluorescence detection, actuation and actuation back to the nominal position 92 is important so as to allow only the fluorescing cell to be sorted and minimize the chance that an errant, non-fluorescing cell be sorted mistakenly. In the nominal case, the flow rate through each channel is roughly 0.2 meter per second. As the cell enters vertical channel 108, it begins fluorescing. The thickness of light channel 88 is chosen to be roughly 30 um, so that the cell is lit by the laser light for 150 us. The fluorescing light is detected in the first 100–200 us, and the actuator is immediately (with small computer/controller delay of only tens of microseconds) moved into position shown as sort position 90. This actuation takes approximately 100 us. Therefore, the actuator is in the sort position just as the cell is approaching the MEMS valve layer 86. MEMS valve layer 86 is also approximately 30 um thick. After actuation from position 92 to 90, the actuator pauses in the sort position for only 100 us, and is then actuated back to position 92. While the actuator can move back without active actuation, simply from relaxation of the spring force, this embodiment uses active retraction to increase speed.

The sort rate of the device is determined by the actuator response time, which is approximately 3.3 kHz. The total time of 300 microseconds includes 100 usec for moving the actuator to the sort position after fluorescence is detected, a 100 usec pause to allow passage of the HSC into the stem cell manifold, and 100 usec for moving the actuator back to the non-sort position. Considering the 1024 such channels, and a velocity of flow in the constricted channels described herein of 0.2 m/sec, the device will pass 1 liter of fluid mixture in 2 hours. The 3.3 kHz sample rate translates into an overall throughput of 3.3 million events/sec, taking into account the 1024 parallel channels. This throughput is almost two orders of magnitude better than the fastest flow cytometers. Typically, the cells are dilute in the fluid mixture, and the number of cells per second will depend on the dilution.

In order to maximize the flow of the fluid mixture without excessive pressures, the MEMS chip utilizes a large number of parallel channels flowing through the plane of the wafer as well as across the plane of the wafer. The large number of short path, parallel channels through the wafer has the advantage that very large pressure gradients are not needed to obtain reasonable flow rates. The device is designed so that the dominant pressure drop is generated in the vertical channel/actuator region only, and care is taken to provide a uniform pressure head preceding the vertical channels and a minimum back pressure after the actuator region as the flow opens up into the larger manifolds. The device also does not need to create or manipulate a fine spray of droplets; instead the flow is continuous. With the actuator acting as a low inertia knife-edge gate valve, relatively low forces are needed to perform the sorting. This keeps the sample rate high with the reasonable voltages applied, on the order of 50 V. The tool is designed to be a low cost, special purpose machine sorting into two buckets only, but the concept is extendable to other applications.

Figure 4:
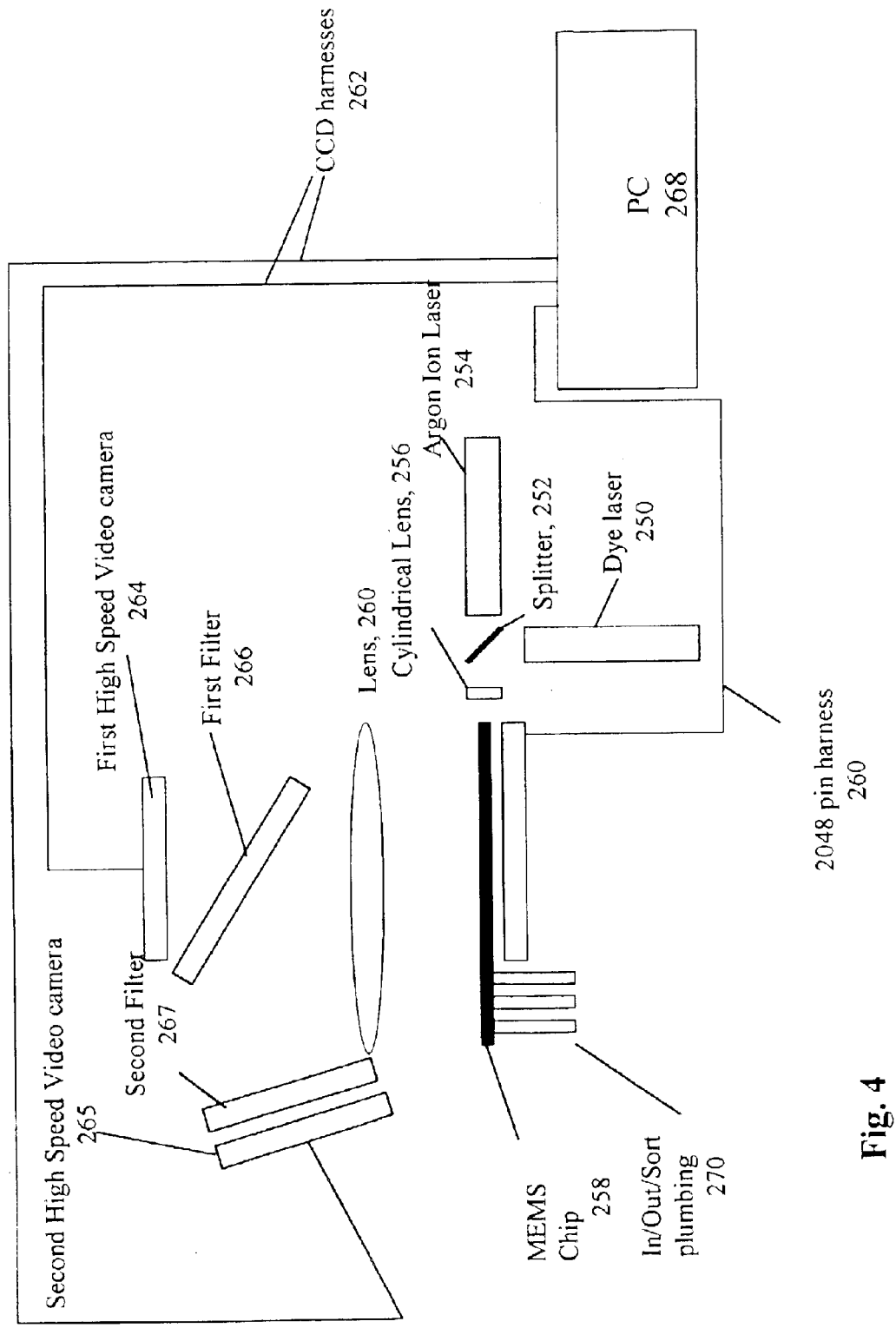
FIG. 4 is a simplified diagrammatic view of the MEMS cell sorter system.

The details of the optical system are shown in FIG. 4. Two lasers are used to allow the flexibility to induce fluorescence in multiple markers: i.e. a first $Ar^+$ laser operating at 488 nm, and the second a Rhodamine 6-G dye laser operating at 590 nm. The beams are combined with a beamsplitter/turning mirror 252, and focused into a line on the light channel 88 by a cylindrical lens 256. The two dimensional sheet of light propagates within the light channel 88. Fluorescent light emanating from vertical channels 108 (if an appropriate fluorescing cell is present) passes out of the MEMS chip through optical cover 80 and the lens 260 directs an image of the chip surface onto the set of CCD cameras 264 and 265, through the set of filters 266 and 267. The filters are used to select only the desired fluorescence signal of the marker. In the case of sorting HSCs in which both CD34 and Thy-1 antigens are used, the filters are selected to pass only the wavelengths for the tags for those antigens, respectively. In general, then, the camera detectors are in the dark except during the rare events of detection of a fluorescence signal. The detection of fluorescence by the CCD array (or the simultaneous detection of both signals, one in each camera) indicates the presence of an HSC in the sample manifold, at the position in the array indicated by the CCD camera. The electronics then causes the appropriate actuator to be energized, diverting the sample cell into the appropriate manifold. The actuator is then positioned back to its initial state.

In the implementation preferred herein, the fluorescent light passing through lens 260 impinges first on one filter, filter 266. Light of the proper wavelength passes through filter 266 into the first high speed video camera 264. All other light reflects from the surface of filter 266, and impinges on filter 267. Light of the proper wavelength for that filter passes through into the second high speed video camera 265. In this way, efficient use is made of the available light to optimize signal-to-noise and speed in the system. A variety of state-of-the-art camera systems are available to serve as the high-speed cameras. For example, Photron USA (San Diego, Calif.) markets the PhotoCAM 250 CL, a monochrome camera with 10,000 frames per second performance (adequate for the 100 micro-second requirement in this invention) with over 4000 pixels in each frame, sufficient for this application. Although this high speed camera is not as sensitive as photo-multiplier tubes commonly used in modern cell-sorters, gain comes from the longer integration time in the current invention, ten times longer than the cell sorters, so that adequate signal-to-noise is achieved using cameras. If additional sensitivity is required for a particular application, an intensifier plate can be added in front of the camera's detector. These are common in industry, known as microchannel plates (MCP), and are an array of channeltrons.

In practice, filters 266 and 267 may not be individual filters, but filters on respective filter wheels, so that one particular filter can be selected simply by rotating the wheel. In this way, the machine can easily be configured to detect different wavelengths.

General-purpose computer 268 directs the operation of the various electronics units through the 2060-pin connector (2048 lines plus 12 ground lines) 260 to control the actuators, and CCD harness 262 to acquire the signal from each camera detector. The general purpose PC also controls laser pulse timing, if a pulsed laser is used. The blood is delivered to the chip and the waste and sorted cells are taken away from the chip through the set of plumbing tubes, 270, typically made of stainless steel, and glued into the MEMS chip.

Figure 5:
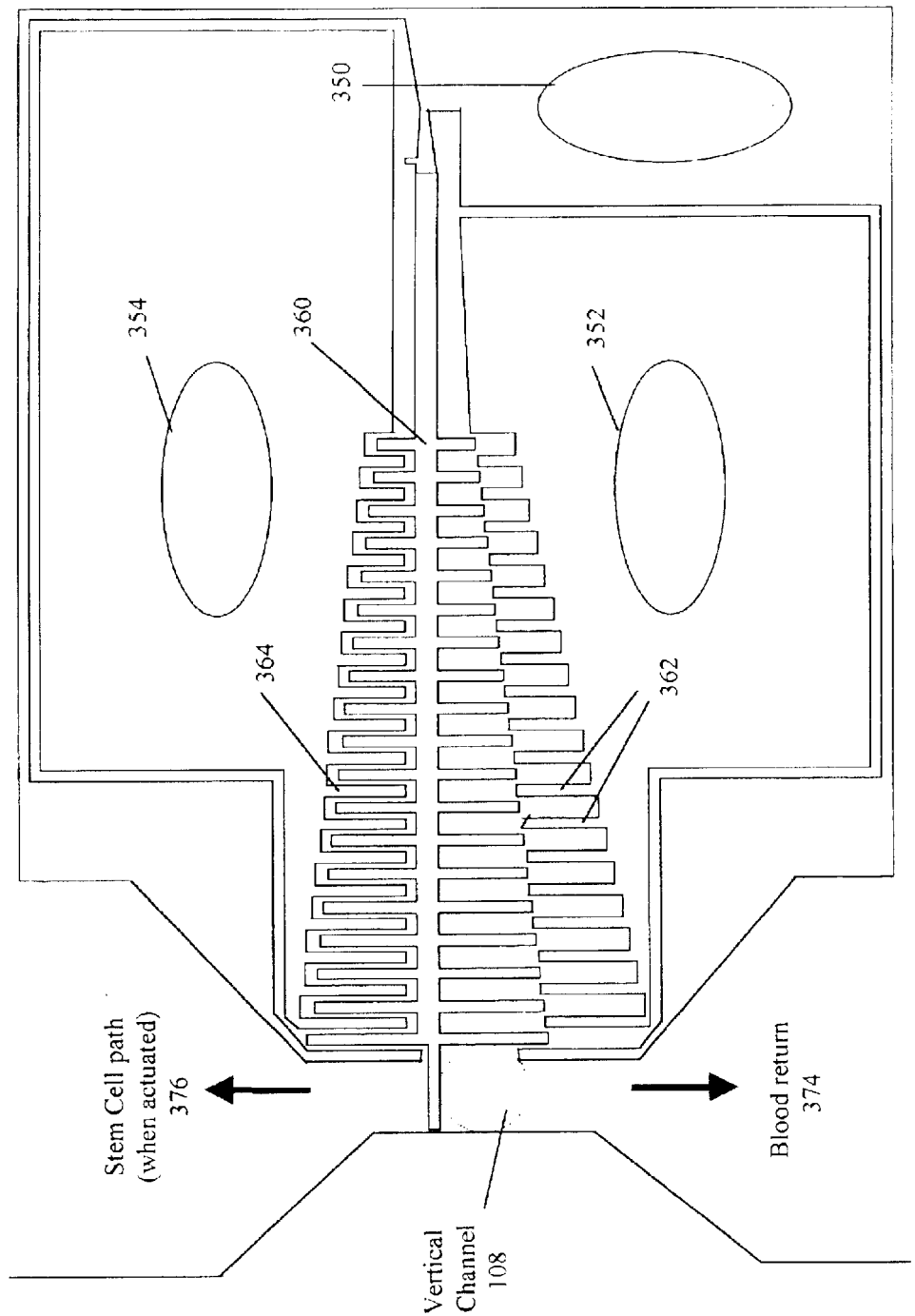
FIG. 5 is an enlarged top-down view of the sorting apparatus, a micromechanical actuator.

The action of the micromechanical actuator can be understood by considering the details of the actuator as seen in FIG. 5. The electrodes are formed in comb shapes 362 and 364 with interlacing fingers on the actuator 360, to increase the surface area and therefore the torque at a given voltage. As shown in FIG. 5, there are three vias and electrical connections to the MEMS valve layer. One via connection 352 is made to comb 362, one 354 is made to comb 364, and the third 350 connects to the moving actuator interlacing fingers 360 as well as to the rest of the silicon layer which is not the interlacing fingers, and can be thought of as the ground of the device. There are twelve ground connections that are brought through the substrate, making the total number of pins out equal to 1024+1024+12=2060. In this way, the fluid mixture is not exposed directly to electric fields; rather the fields are isolated between the comb area and the interlacing fingers of the actuator. Sub-micron lithography yields very sharp features, with high surface energy corners and gaps of less than 2 um, too small to allow a HSC flowing in from the vertical channel 108, to leak between the combs. The valve is normally in the position to direct flow into the waste manifold 374, but can be actuated within 100 us to redirect the flow into the stem cell manifold 376.

A requirement of the actuator is that it have sufficient force to withstand the pressure of the fluid mixture and hold its proper position, directing flow into the appropriate manifold. Straightforward fluid calculations show that forces on the order of 10e−9 N are required, and these are easily attained with the current electrostatic actuator configuration. The action can be seen in the top-down view shown in the figure, with the sample cell entering the actuator area from the top through the vertical inlet 108, and flowing downward into the waste receptacle, as the actuator blocks the upward path leading to the stem cell manifold. In the actuated state however, the actuator 360 is drawn down by electrostatic attraction to the lower comb 362, closing off the lower route to the waste receptacle and opening the upper route to the stem cell manifold. The hinge area of the actuator is designed to have the restoring force required to return the actuator to its starting position at the upper comb, and separated from the lower comb, closing the stem cell path and opening the path to the waste manifold and receptacle. In our preferred embodiment, however, we include a second upper comb electrode, 364, to retract the actuator to its original position. When a voltage is applied to upper comb 364, the valve is retracted within approximately 100 us to the normal position, which directs the flow once again to the waste manifold 374.

It should be pointed out that at all times, independent of the position of each valve/actuator, the saline solution which makes up the bulk of the fluid mixture is flowing into both the waste manifold 374 as well as the stem cell manifold 376. This is because of the approximate 1 micron gaps which exist between the valve and the light channel 88, between the actuator gate and the sidewall of the manifold, and between the actuator gate and the silicon substrate 94. This continuous flow does not act to the detriment of the device, however, since the gaps are much smaller than the size of the cells to be sorted. This is evident for the case of HSCs (5 to 10 um in diameter and roughly round). If the cells to be sorted are very small, nearing 1 um, then greater care would have to be taken to decrease the gaps. For example, 0.3 um resolution lithography is readily available, although not widely used in MEMS technology, and can be applied to reduce the gaps involved here, as well as reduced thickness wafer bonding lines and insulator thickness on the silicon-on-insulator (SOI) wafer which comprises the actuator wafer.

To discourage wetting of the wafer surfaces, the actuator valve wafer is coated with a thin fluorocarbon film, approximately 10 to 20 Angstroms thick, and with some bonding affinity for the wafer surface. Examples of the fluorocarbon material include AM2001 or Z-Dol, common lubricants sold by Dupont Corp. (Wilmington, Del.). Coating with such films is common in industry, for example it is used on thin-film disks for disk-drive storage. The function of the fluorocarbon film is to reduce wetting of the wafer surfaces. While the fluid mixture is driven by pressure through vertical channels 108, past the valve and into one of the manifolds 376 or 374, the fluid mixture will not wet or flow easily into the comb region defined by the actuator 360 and the upper and lower combs 362 and 364. Fluid mixture in this region is not desired, as the fluid is conductive as well as being viscous. The conductivity will interfere with the resulting electrostatic force generated by applying a voltage to the interlacing fingers, and the viscosity will slow down the actuator speed. In the event that there is too much leakage of the fluid mixture into the interlacing finger area and the device function suffers for a particular application, pressurized gas (air, nitrogen, for example) can be provided to the MEMS chip through a via in the bottom of the chip, with slight overpressure to keep the interlacing region dry.

The blood enters the MEMS chip from a regulated pressure supply through 2 filters, a first small pass filter at 20 um, and a subsequent large pass filter at 3 um. The filters assure the particles are within the expected size range, and filters out debris which could otherwise clog the small passageways. The output of the filters feeds the MEMS sorting chip. The plumbing lines, which contain the flow, are bonded permanently to the chip, making the package entirely disposable. Sterilization is therefore not an issue.

The MEMS chip is created by standard processing now common in the MEMS industry. The MEMS chip is made by making two separate wafers, the actuator wafer and the optical wafer, bonding these wafers together, and subsequently dicing the wafer into constituent dies, which are the MEMS chips. For example, for a 6" diameter wafer, each wafer comprises approximately 40 to 50 MEMS chips.

The optical wafer includes optical cover 80, spacer 82, void 83, and light channel 88, as shown in FIG. 1, and is made as follows. The wafer starts as a 640 micron-thick, 6" diameter, silicon dioxide (glass) wafer, widely available. As the optical wavelengths considered herein are within the visible range, normal fused quartz glass wafers will suffice. If the wavelengths demanded transmission in the ultraviolet, for example, single crystal $SiO_2$ could be used. Spacer 82 is then formed by depositing the spacer material (e.g. sputtered $SiO_2$, silicon nitride, plated NiFe), typically 30 to 40 microns thick, patterning lithographically, and then etching the spacer material where it is not required. The region, which will become void 83 is then made by plating a sacrificial material (such as copper) into the void 83 region. The plating is performed much thicker than is required to fill up the void 83 space, and the wafer is lapped flat with chemical mechanical polishing, using spacer 82 as a lapping stop. The sacrificial material is chosen in this case to lap much faster than spacer 82, and thus the wafer is made flat with spacer 82 and the sacrificial material filling void 83 exposed. Light reflecting layer 198 is then formed by depositing a material such as chromium, gold, or titanium, (chromium is preferred in this embodiment) and the layer is approximately 1000 Angstroms thick. The optically transparent layer, light channel 88 is then deposited, and could be either $SiO_2$ or $Al_2O_3$, with sputtered $SiO_2$ preferred in this embodiment, approximately 30 microns thick. Then light reflecting layer 199 is deposited, again 1000 Angstroms of chromium in the preferred embodiment.

One of the two materials making up the eutectic wafer-bonding material, eutectic 99, is then deposited and patterned. For example, the preferred material is a gold-indium eutectic, and so 1000 Angstroms of gold is deposited everywhere. The optical wafer is then patterned and etched to remove the gold, chrome, glass and other chrome layer in the region of vertical channels 108 and the inlet via 96. The patterning is standard photolithography, and the etching can be done either with wet etchants or reactive ion etching (RIE). The preferred embodiment herein is RIE, as the wall angles are very controllable and the chemistries are well known and practiced. The wall angle is chosen to be slightly off vertical, with the narrow section at the top of the vertical channels 108 to avoid the possibility of a particle becoming trapped inside the channel. Lastly, the optical wafer is completed by etching away the sacrificial material, leaving void 83 empty. In the preferred embodiment, the sacrificial material is copper, and it can be removed by exposure to a liquid etchant.

The actuator wafer is built starting with an SOI wafer (silicon-on-insulator). The starting material is 640 micron-thick silicon, highly resistive in our preferred embodiment using very low doping such as float-zone silicon, with a 1 micron $SiO_2$ layer sandwiched between the thick silicon and an "active layer" silicon wafer. The active layer is chosen to be approximately 30 microns thick. In this case. The electrical vias are formed first, by patterning the back of the actuator wafer, using deep reactive ion etching (DRIE) to etch vertical walls in the silicon all the way to the $SiO_2$ etch stop. The $SiO_2$ is removed at the bottom of the vias using RIE or wet chemistry (brief hydro-fluoric acid dip), a plating-base is sputtered or deposited by ion-beam deposition (1000 Angstroms of copper) and copper is plated into the holes, filling them beyond the surface of the actuator wafer. The surface is then lapped with chemical mechanical polishing until flat, leaving the copper flush with the wafer surface backside.

Blood In, Blood Return, and Cell Sorting channels are also etched into the actuator wafer substrate using patterning and DRIE etching.

The front side of the actuator wafer, which is the "active layer" silicon of 30 microns thickness, is then patterned and etched with DRIE, forming the actuator, interlacing combs, inlet via, stem cell manifold and blood return manifold with one etch. The etch stop is the 1 micron-thick $SiO_2$ layer of the original SOI sandwich. The other component of the eutectic is then applied by patterning and plating 1 micron of indium in our preferred embodiment. The pattern is such that the indium makes a seal against the optical wafer in all areas except the moving actuator gate. In that area, there is no indium, and so the indium provides both one component of the eutectic seal as well as the thin standoff allowing actuator movement. The eutectic bond line between the optical wafer and actuator wafer also serves as the grounding connection between the 1024 actuators. The $SiO_2$ layer is then etched to free the actuator, preferably using a brief hydro-fluoric acid dip, well known the MEMS art. The actuator wafer is then dipped in a highly-dilute fluorocarbon mixture (AM2001 from Dupont Corporation is the preferred embodiment) to apply a 15 Angstrom layer of the lubricant over the surface.

The optical and actuator wafers are then bonded together using a Wafer Bonder, typically a Karl-Suss (Waterbury Center, Vt.) aligner/bonder, in which the temperature is chosen to enable the two materials chosen to form a eutectic bond. In the case of indium and gold used here, a temperature of 180 degrees centigrade will suffice.

On the bottom side of the actuator wafer, standard bumping processes on the exposed copper vias can be used to create a ball grid array for surface or board mount applications. Therefore the design has the advantage of bonding the transmission lines of the device directly to the input lines, avoiding the impedance mismatch associated with wire bonding. The vias can also be used for wire bonding pads for situations where surface mount technology cannot be used.

Setup and operation of the MEMS chip and system described is as follows: the MEMS chip is placed onto the pin array structure with pin harness. A sample fluid mixture of saline solution and dilute 5um beads with the proper attached fluorescent markers for the anticipated cell sorting is then applied to the chip. The lasers irradiate the fluid as it enters the vertical channels, and the resulting fluorescence is collected by the lens and imaged onto the CCD cameras. The computer then integrates the output of the video signal and identifies the exact position of the vertical channels 108, as imaged by the lens/filter/camera. In this way, the system can adapt to some variability in the exact alignment of the disposable chip in its receptor. After the sample fluid is flushed from the chip, the system is ready to sort cells.

The invention described herein has several features, which enhance its reliability. In order to sort biological cells and contemplate treatment for cancers, etc., the system must be considered to be very safe in sorting, that is the chances of mistakenly sorting a cancer cell must be very low. The fail-safe position of each actuator/valve for the MEMS chip is to not sort the cell. If any actuator fails to function, it constitutes only a slight loss in efficiency of sorting (for example, one non-functioning actuator represents only 0.1% loss in efficiency in the current configuration), but does not pose a risk to the patient constituted by sorting the wrong cell. Similarly, the software running in the general-purpose computer has fail-safe features. For example, if the fluorescent signal from a single vertical channel 108 remains on for more than approximately 400 microseconds, then that actuator is disabled, since that particular channel may have become clogged, and one cannot take the risk of allowing an improper cell to be sorted mistakenly.

While the invention has been particularly described and illustrated with reference to a preferred embodiment, it will be understood by those skilled in the art that changes in the description and illustrations may be made with respect to form and detail without departing from the spirit and scope of the invention. For example the electrostatic forces may be manipulated by choice of film thicknesses, hinge design and material composition. Alternatively, electromagnetic forces, piezo-electric forces or thermal expansion forces could be substituted for electrostatic forces. Spring constants may be varied by changing the aspect ratio of the beams or stiffnesses of the hinges. The device described can be used to sort any molecule, which has been tagged with an appropriate fluorescent marker. Accordingly, the present invention is to be considered as encompassing all modifications and variations coming within the scope defined by the following claims.

I claim:

1. A micromechanical cell sorting chip, comprising:
   a plurality of hingedly mounted driven members defined on a fabrication substrate having proximal ends and distal ends;
   an optically transparent layer having a top surface, covering the hingedly mounted driven members, but allowing clearance for their movement, and containing a plurality of vertical channels located at the distal ends of the hingedly mounted driven members for delivering a fluid mixture of cells from the top surface to the distal ends of said hingedly mounted members;
   an inlet via for delivering the fluid mixture of cells to the top surface of the optically transparent layer;
   an optical cover glass covering the optically transparent layer, and thereby forming a fluid flow channel between the cover glass and the top surface of the optically transparent layer;
   a set of microfluidic channels formed in said fabrication substrate, providing a number of exit paths for the fluid mixture of cells;
   an actuation means for actuating said hingedly mounted members in order to direct the fluid mixture along one of the number of exit paths, according to a fluorescence signal detected from the fluid mixture of cells while in or above the vertical channel.

2. The micromechanical cell sorting chip of claim 1, wherein the signal detected is laser-induced fluorescence from a fluorescent marker attached to a component of interest in the fluid mixture of cells.

3. The micromechanical cell sorting chip of claim 2, wherein the component of interest in the fluid mixture of cells is a human hematopoietic stem cell population subset.

4. The micromechanical cell sorting chip of claim 2, wherein the component of interest in the fluid mixture of cells is a virus cell population.

5. The micromechanical cell sorting chip of claim 2, wherein the hingedly mounted members are covered by a thin layer of fluorocarbon lubricant.

6. The micromechanical cell sorting chip of claim 2, wherein the actuation means is electrostatic.

7. The micromechanical cell sorting chip of claim 6, wherein one or more of the hingedly mounted driven members form one or more respective capacitor plates.

8. The micromechanical cell sorting chip of claim 7, wherein at least one of the hingedly mounted driven members is caused to deflect toward at least one of the capacitor plates by the application of a voltage between the driven member and the capacitor plate, thereby directing the component of interest in the fluid mixture of cells into one of the number of exit paths.

9. The micromechanical cell sorting chip of claim 8, wherein electrical access to the capacitor plates is gained with through holes formed in the fabrication substrate, and the through holes are deposited with conducting material.

* * * * *